(12) United States Patent
Zappala

(10) Patent No.: US 6,328,734 B1
(45) Date of Patent: Dec. 11, 2001

(54) FLEXIBLE ENDOSCOPE WITH BIPOLAR RETURN ELECTRODE AND WORKING CHANNEL

(76) Inventor: Stephen M. Zappala, 98 Rattlesnake Hill Rd., Andover, MA (US) 01810

( * ) Notice: Subject to any disclaimer, the term of this patent is extended or adjusted under 35 U.S.C. 154(b) by 0 days.

(21) Appl. No.: 09/407,811

(22) Filed: Sep. 28, 1999

Related U.S. Application Data

(60) Provisional application No. 60/102,806, filed on Oct. 2, 1998.
(51) Int. Cl.⁷ .................................................. A61B 18/16
(52) U.S. Cl. .............................................. 606/32; 606/46
(58) Field of Search .................................. 606/46, 48, 50, 606/32

(56) References Cited

U.S. PATENT DOCUMENTS

| | | | |
|---|---|---|---|
| 4,116,198 | * | 9/1978 | Roos ........................................ 606/46 |
| 4,184,492 | * | 1/1980 | Meinke et al. ........................... 606/46 |
| 4,311,144 | * | 1/1982 | Harada ..................................... 606/46 |
| 4,606,331 | * | 8/1986 | Shene ....................................... 606/46 |
| 5,885,277 | * | 3/1999 | Korth ....................................... 606/46 |

\* cited by examiner

*Primary Examiner*—Lee Cohen
(74) *Attorney, Agent, or Firm*—Mirick, O'Connell, DeMallie & Lougee, LLP

(57) ABSTRACT

An endoscopic device adapted for use in both diagnostic and therapeutic procedures, comprising, one or more sheaths; one or more endoscopes disposed within the sheath; one or more return electrodes disposed within the sheath; and one or more working channels disposed within the sheath.

10 Claims, 4 Drawing Sheets

FLEXIBLE ENDOSCOPE WITH BIPOLAR RETURN ELECTRODE AND WORKING CHANNEL

This application claim benefit to Provisional Application No. 60/102,806 filed Oct. 2, 1998.

FIELD OF THE INVENTION

This invention relates to endoscopes and more specifically to an endoscope which can be used as a diagnostic instrument and a therapeutic device.

BACKGROUND OF THE INVENTION

Endoscopes, which accommodate a bipolar energy source and which deliver the electrosurgical radiofrequency within a saline medium, are known in the art. However, interruption of the irrigation flow in such endoscopes may cause severe thermal injury to the surrounding tissues. Moreover, utilization of the preferred irrigating media, physiologic 0.9N saline, with an endoscope using a standard monopolar energy source is not feasible because a substantial portion of the radiofrequency energy from an electrosurgical generator unit, (ESU), to the endoscope, is dissipated within the ionic nature of the sodium chloride. To avoid dissipation, more non-conducting irrigation solutions are used such as water, glycine or sorbitol. However, these latter solutions may cause hyponatremia. Thus, use of monopolar energy has fallen out of favor with most endoscopic surgeons, whether they are performing urologic, gynecologic, arthroscopic or laparoscopic procedures.

In addition, endoscopes to date are not adapted to act as combined diagnostic and therapeutic instruments, and endoscopes that utilize a radiofrequency energy source generally require a ground-dispersive pad. These ground pads increase costs and may cause flesh burns.

SUMMARY OF THE INVENTION

It is therefore a primary object of this invention to provide an endoscope which provides bipolar capabilities without the risk of thermal injury.

It is a further object of this invention to provide an endoscope which enables a physician to use a physiological saline solution as the irrigant without problems associated with dissipating electrosurgical energy.

It is a further object of this invention to provide an endoscope which can be used for both diagnostic and therapeutic procedures.

It is a further object of this invention to provide an endoscope with a bipolar return electrode and a working channel.

It is a further object of this invention to provide an endoscope with a coaxial electrode which does not require a ground-dispersive pad.

It is a further object of this invention to provide an endoscope with a bipolar return electrode and a working channel through which items such as grasping and biopsy forceps, radiofrequency energy or injectables may be passed.

It is a further object of this invention to provide an endoscope in which the outflowing irrigant is used to cool the coaxial cable of a bipolar resecting device.

It is a further object of this invention to provide an endoscope which provides more energy to a cutting loop and thus more heat, which in turn provides quicker and more efficient tissue removal and improved cauterization.

It is a further object of this invention to provide an endoscope with a bipolar return electrode and a working channel with which conductive physiologic irrigation solution may be used.

The preferred embodiment of the endoscopic device of the invention adapted for use in diagnostic and therapeutic procedures, comprises: one or more sheaths; one or more endoscopes disposed within the sheath; one or more return electrodes disposed within the sheath; and one or more working channels disposed within the sheath. The endoscopic device may further comprise one or more irrigation channels disposed within the sheath capable of transporting one or more irrigation fluids through the channel; and a coaxial cable, disposed within the sheath, in which one or more of the return electrodes is disposed so that one or more of the electrodes surrounds one or more of the irrigation channels so that the irrigation fluid is capable of cooling the return electrode. The endoscopic device also preferably comprises an electrical conductor disposed within the working channel, one or more light source channels, and/or a means for steering.

Another preferred embodiment of the endoscopic device of the invention that is capable of use as both a diagnostic instrument and a therapeutic device, wherein at least a portion of the device is disposed within a sheath, comprises: one or more lenses, one or more internal working channels; and one or more internal bipolar return electrodes. Similarly, this embodiment may also comprise a coaxial cable comprising at least one irrigation channel, wherein at least one of the return electrodes is disposed within the cable and wherein the irrigation channel is capable of cooling the return electrode. Further, at least one of the working channels may carry one or more items selected from a group consisting of forceps, one or more electrical conductors and one or more injectables.

The invention may utilize any type or size endoscope used to perform urologic, gynecologic, arthroscopic or laparoscopic procedures, including but not limited to cystoscopes, gastroscopes, colonoscopes, hysteroscopes and choledocoscopes.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS

Figure 1:
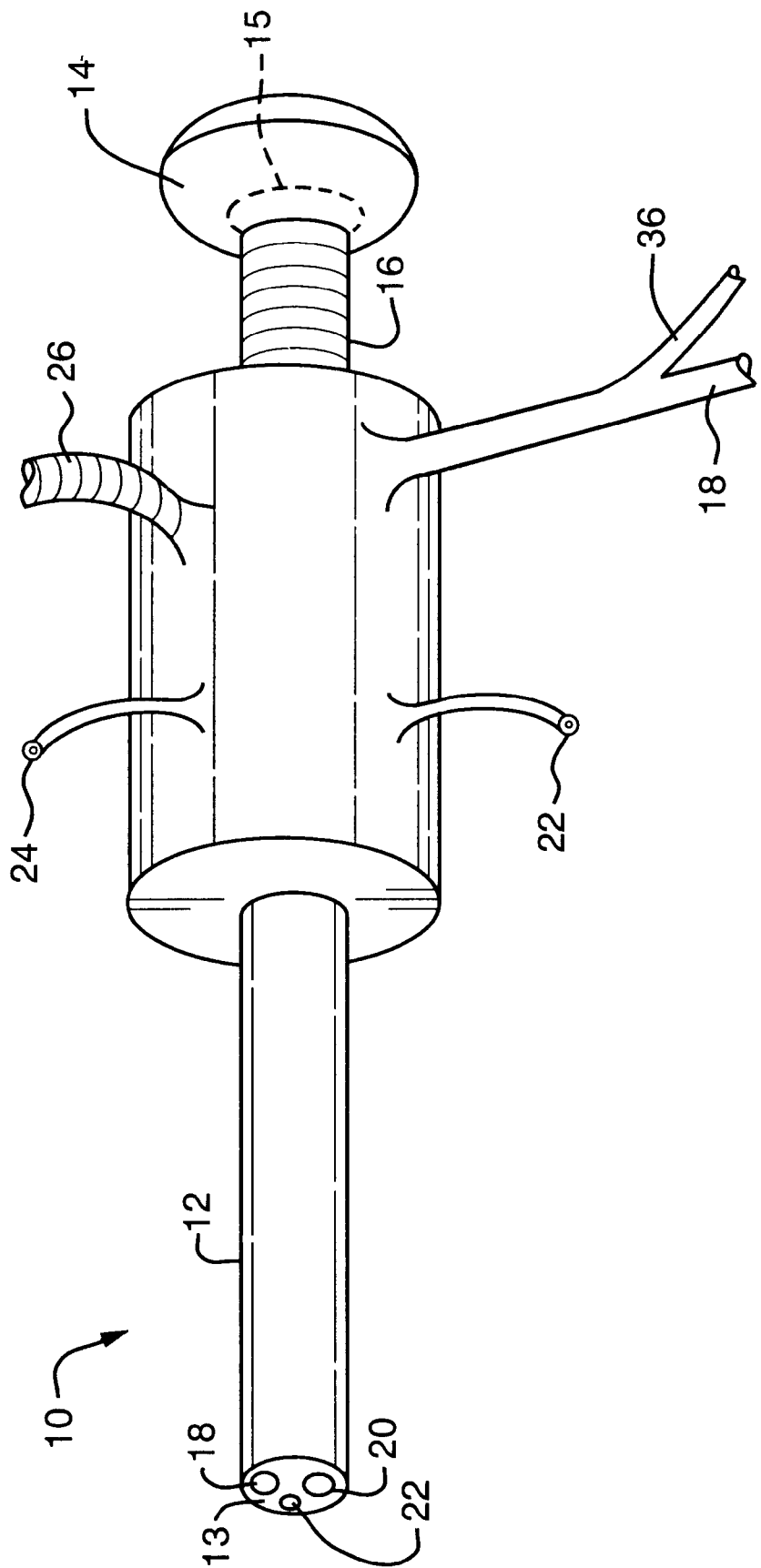
FIG. 1 is a perspective view of the preferred embodiment of the device of this invention.
Figure 2:
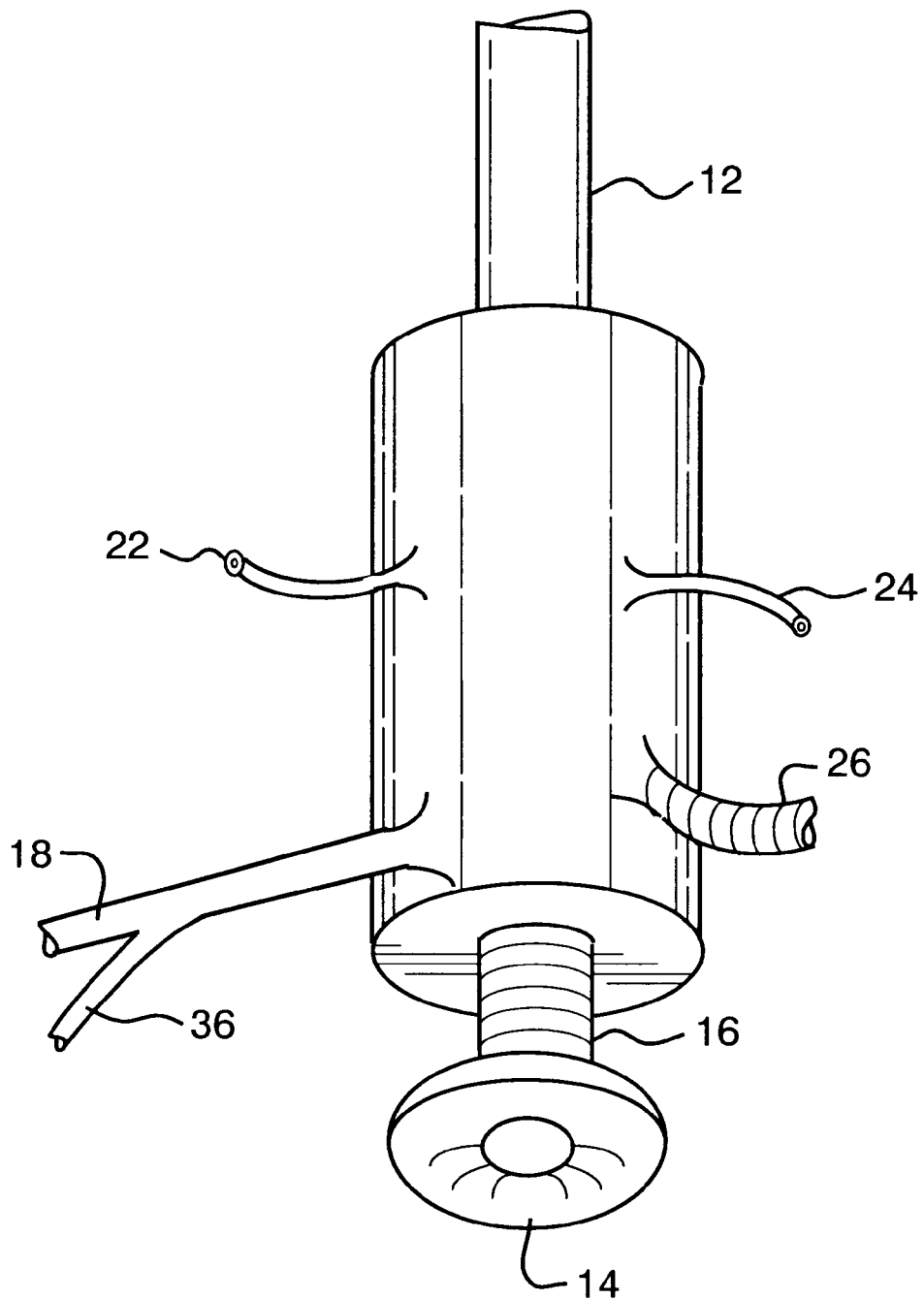
FIG. 2 is a perspective view depicting the physician end (proximal end) of the device of FIG. 1.
Figure 3:
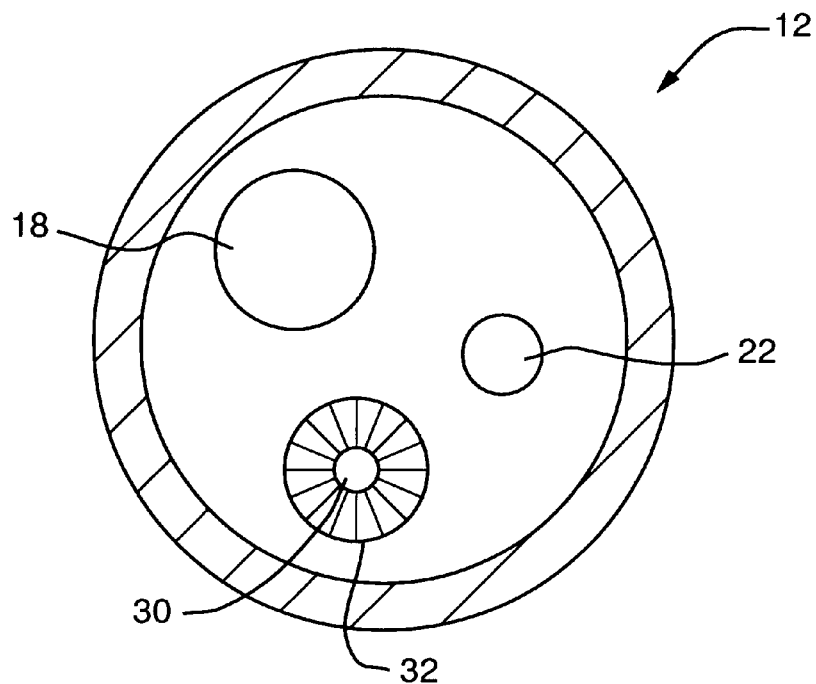
FIG. 3 is a cross-sectional view taken through the shaft of the device of FIG. 1.

The endoscope of the invention for use as both a diagnostic instrument and a therapeutic device is designed for a physician's out-patient site. FIG. 1 illustrates a preferred embodiment of the multi-channel device of the invention, generally referred to as device 10, which is adapted for use with an electrosurgical generator unit (ESU). The device of the invention will enable an endoscopist to cauterize tumors and lesions and biopsy a site without the additional need for a ground dispersive pad. An internal coaxial cable will function as the return electrode for the radiofrequency energy delivered through a separate working channel. The internally located return electrode allows the endoscopist to use physiologic saline as the irrigating fluid because the energy will be transmitted at the surgical site from the tip of the cauterizing electrode to the return electrode located in the coaxial cable.

At least shaft 12 of device 10 is encased in outer sheath 28 which may comprise stainless steel and/or a hydrophilic coated silastic which defines a central hollow core 13 into which a variety of standard endoscopes would fit, including, but not limited to, cystoscopes, gastroscopes, colonoscopes, hysteroscopes and choledocoscopes. Suitable endoscopes are readily available from companies such as Storz, Olympus, Wolf and ACMI. The sheath of the invention is designed to engage any of these endoscopes in a manner which would be understood by someone of ordinary skill in the art using a locking mechanism.

The endoscope depicted in the drawings, endoscope 14 is a 35 cm cystoscope having an outer diameter of about 16 Fr, although, as noted, the invention may be adapted for any type of endoscope. The length of device 10 will vary depending on the primary surgical subspecialty requirements and the endoscope used. Endoscope 14 may be focused with focusing means 16 commonly known in the art and typically includes a steering device known in the art such as steering device 26.

Figure 4:
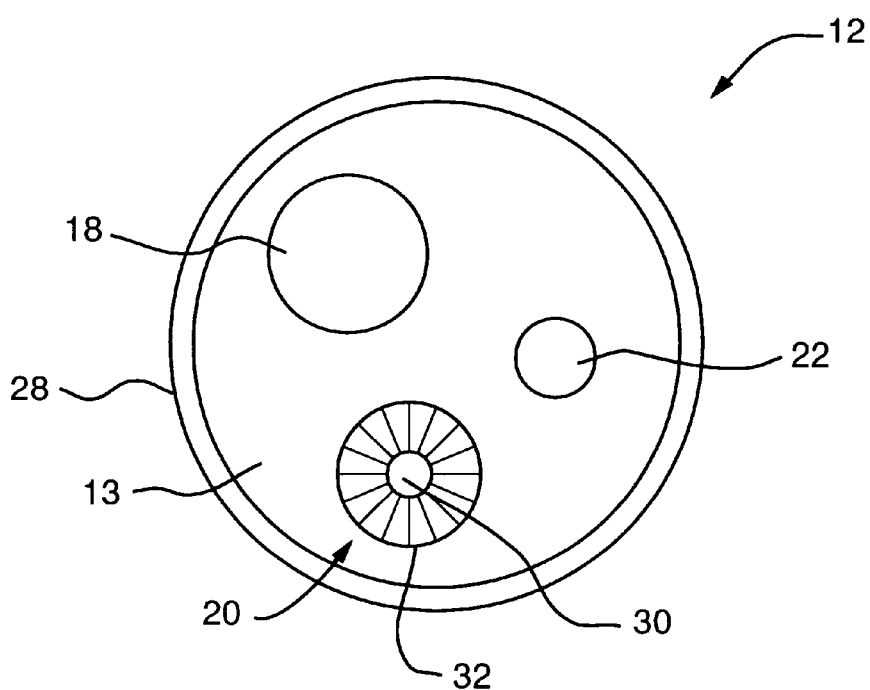
FIG. 4 is an end view of the patient end (distal end) of the device of FIG. 1.
Figure 5:
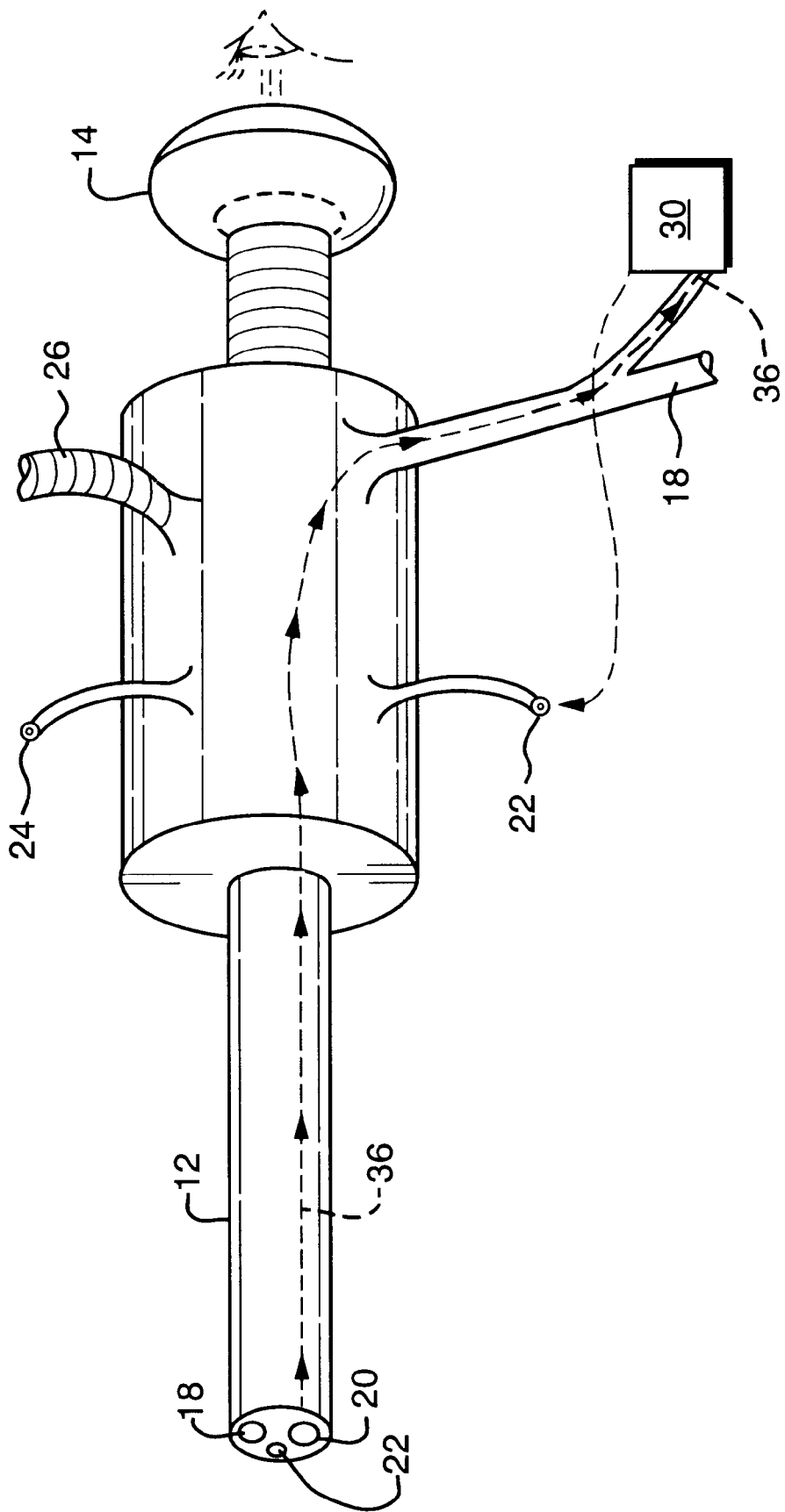
FIG. 5 is a schematic view of the device of FIG. 1 in use.

As shown in FIG. 4, sheath 28 defines all inner tubular space 13 having an inner diameter of sufficient size to serve as a sleeve around endoscope 14. The diameter of sheath 28 may taper down from the proximal end to the distal end. Sheath 28 also contains within its inner tubular space, a plurality of channels, e.g. channels 18, 20, and 22. Channel 18 is a fiber optic channel for carrying light from a xenon light source located near the proximal end of the device to the surgical site. Channel 22 is a working channel which enables the device of the invention to be used as a therapeutic device, as well as the diagnostic instrument by virtue of the endoscope. Working channel 22 enables the passage of items such as grasping or biopsy forceps, radiofrequency energy using an energy conducting loop, and/or injectables. The term injectable is used in its broadest sense and includes, but is not limited to, any liquid or solid item capable of being injected through the working channel. Working channel 22 is preferably has an inner diameter of about 3 Fr.

Channel 20 is preferably a coaxial cable through which electrical conductor 32 is concentrically located around irrigation channel 30. Electrical conductor 32 acts as the bipolar return electrode or path for the electrosurgical energy which has been supplied by electricalsurgical generator unit 34 and transmitted to the surgical site by a conductor, such as a loop, (not shown), which is fed through working channel 22. The bipolar return path is housed within device 10 to prevent direct coaptation between the energy from the ESU and the patient's tissue. Irrigation channel 30 preferably transports a physiologic saline irrigant, although a standard irrigant such as glycine, sorbitol or water can be used, to and from, respectively, the surgical site. Endoscope 14 typically includes ocular lens 15 at the proximal end of endoscope 14 and a surgical site lens (not shown) proximate the distal end of endoscope 14.

Irrigation channel 30 is provided with the irrigant inflow at the proximal end of the device and irrigation channel 30 is preferably used to carry the irrigant suction or outflow away from the surgical site at the distal end of the device. Any resistive heating of conductor 32 is dissipated by the irrigant flowing through irrigation channel 30 because irrigant flowing through channel 30 hydrocools the return electrode, thus protecting surrounding tissue and the device from thermal damage. Conductor 32 is preferably a coaxial cable provided with external cord 36 for connecting conductor 32 with ESU 34. Sheath 28, together with the coaxial cable, enables a physician to utilize a physiologic saline solution as the irrigant, instead of water, glycine or sorbitol, because the internal coaxial cable acts as a return electrode which allows ESU 34 to act as a bipolar energy source. This design solves the problem of energy dissipation associated with an ionic saline irrigant when used in connection with a monopolar energy source and a standard ground dispersion pad.

An optical video system in conjunction with continuous flow may be used. Normal saline and a fluid warmer delivers the irrigant at a height approximately 60 cm above the operative field.

The sheath of the invention functions to disperse the monopolar oscillating radio frequency wave from the ESU. The current path travels from the active loop electrode, through the tissue at the surgical site and also through the saline, subsequently traversing the bipolar sleeve and returning to the ESU. The bipolar sleeve is thus defined as a return electrode. Thus, a dispersive ground pad is not necessary since the current path travels through the sleeve and the ionic effects of the saline irrigant are minimized. It is imperative that any tissue to be biopsied or otherwise removed be interposed between the endoscope loop and the bipolar sleeve in order to optimize the cutting efficacy. The surrounding tissue is insulated from the conductive component of the sleeve by its outer insulation. Use of the sheath of the invention does not mandate any selection parameters on the physician based upon anatomy. The sheath may be used using direct vision and does not require ancillary imaging systems.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. An endoscopic device adapted for use in diagnostic and therapeutic procedures, comprising,
   one or more concentric sheaths of which an innermost sheath has a central hollow core;
   one or more endoscopes disposed within said hollow core;
   one or more working channels disposed within said hollow core;
   at least one coaxial cable, disposed within said hollow core, wherein at least one return electrode surrounds a return irrigation channel through which return irrigation fluid is adapted to flow and cool said return electrode.

2. The endoscopic device of claim 1, further comprising an electrical conductor disposed within one of said working channels.

3. The endoscopic device of claim 1, further comprising one or more light source channels disposed within said hollow core.

4. The endoscopic device of claim 1, further comprising a means for steering at least one of said endoscopes.

5. The endoscopic device of claim 1, wherein at least one of said endoscopes is a cystoscope.

6. An endoscopic device capable of use as both a diagnostic instrument and a therapeutic device, comprising,
- a sheath;
- one or more endoscopes disposed at least partially through said sheath;
- one or more working channels disposed at least partially through said sheath; and
- a coaxial cable, disposed at least partially through said sheath, comprising a first irrigation channel and at least one return electrode disposed about said first irrigation channel, whereby irrigation fluid, flowing through said first irrigation channel from a distal end of said sheath to a proximal end of said sheath, is adapted to cool said return electrode.

7. The endoscopic device of claim 6, wherein at least one of said working channels carries one or more items selected from a group consisting of forceps, one or more electrical conductors and one or more injectables.

8. The endoscopic device of claim 6, further comprising a second irrigation channel, disposed at least partially through said sheath, for transporting a physiologic saline irrigant from said proximal end of said sheath to said distal end of said sheath.

9. The endoscopic device of claim 6, wherein one or more of said endoscopes is selected from a group consisting of cytoscopes, gastroscopes, colonoscopes, hysteroscopes and choledocoscopes.

10. The endoscopic device of claim 9, wherein one or more of said endoscopes is a cystoscope.

* * * * *